United States Patent [19]

Findlay et al.

[11] Patent Number: 4,788,140

[45] Date of Patent: Nov. 29, 1988

[54] ANALYTICAL ELEMENT CONTAINING PHOTOSENSITIVE COMPOUND AND FILTER LAYER AND METHOD OF USE

[75] Inventors: John B. Findlay; Brent A. Burdick; Ronald A. Wellman, all of Rochester; Mark E. Shafer, Fairport, all of N.Y.

[73] Assignee: Eastman Kodak Company, Rochester, N.Y.

[21] Appl. No.: 830,036

[22] Filed: Feb. 18, 1986

[51] Int. Cl.$^4$ .................. C12Q 1/50; C12Q 1/28; G01N 1/48

[52] U.S. Cl. ........................... 435/17; 435/7; 435/28; 435/805; 422/56

[58] Field of Search ............... 435/7, 17, 28, 805; 422/56

[56] References Cited

U.S. PATENT DOCUMENTS

| | | | |
|---|---|---|---|
| 4,042,335 | 8/1977 | Clement | 23/253 |
| 4,089,747 | 5/1978 | Bruschi | 195/99 |
| 4,144,306 | 3/1979 | Figueras | 422/56 |
| 4,166,093 | 8/1979 | Smith-Lewis et al. | 422/56 |
| 4,237,044 | 12/1987 | Würzburg et al. | 530/387 |
| 4,387,160 | 6/1983 | Gomez et al. | 435/7 |
| 4,430,436 | 2/1984 | Koyama et al. | 422/57 |
| 4,478,944 | 10/1984 | Gross et al. | 435/805 |
| 4,547,461 | 10/1985 | Esders et al. | 435/17 |

*Primary Examiner*—Robert J. Warden
*Assistant Examiner*—Janelle Graeter
*Attorney, Agent, or Firm*—J. Lanny Tucker

[57] ABSTRACT

A multilayer analytical element for the determination of a clinically significant enzyme analyte comprises a photosensitive compound (e.g. a photosensitive dye or dye precursor) and a filter layer containing one or more filter dyes. The filter layer is situated in the element such that incident radiation used to detect a density change resulting from interaction of the analyte and the photosensitive compound passes through the filter layer before it reaches the photosensitive compound. The use of the filter layer inhibits premature changes in the photosensitive compound caused by incident radiation. This element is particularly useful for the determination of creatine kinase or one of its isoenzymes, e.g. creatine kinase-MB.

20 Claims, 2 Drawing Sheets

ANALYTICAL ELEMENT CONTAINING PHOTOSENSITIVE COMPOUND AND FILTER LAYER AND METHOD OF USE

FIELD OF THE INVENTION

The present invention relates to clinical chemistry. In particular, it relates to a multilayer analytical element useful for determination of clinically significant enzyme analytes, e.g. lipase, creatine kinase or an isoenzyme thereof. This invention also relates to a method of using such an analytical element.

BACKGROUND OF THE INVENTION

Colorimetric assays of various fluids for the determination of chemical or biological substances (identified as analytes herein) are well known. Such assays are particularly important in clinical chemistry as the medical and veterinary professions attempt to rapidly and economically diagnose and treat ailments in humans and animals. As a result, researchers are continually searching for more sensitive and less expensive means for doing such assays.

A relatively recent contribution to the clinical chemistry art was the development of thin-film multilayer analytical elements such as those described, for example, in U.S. Pat. Nos. 3,992,158 (issued Nov. 16, 1976 to Przybylowicz et al) and 4,144,306 (issued Mar. 13, 1979 to Figueras). Those elements are generally described as having a porous spreading layer, a reagent layer and a registration layer carried on a nonporous support. The support may be designed to transmit all or part of incident radiation in order to facilitate measurement of detectable species at particular wavelengths.

Another significant advance in the art is described in U.S. Pat. No. 4,089,747 (issued May 16, 1978 to Bruschi). This reference describes certain triarylimidazole leuco dyes which have become very useful in assays for hydrogen peroxide or glucose, uric acid and other analytes where hydrogen peroxide is generated as a result of the presence of the analyte.

The determination of the activity of creatine kinase (abbreviated herein to CK, but also known at creatine phosphokinase, CPK, or ATP:creatine phosphotransferase E.C.2.7.3.2.) in human serum is considered one of the most sensitive laboratory methods for diagnosing diseases of skeletal muscles and diseases of the myocardium. CK determinations are useful, for example, for diagnosis of progressive muscular dystrophy, dermatomyositis and especially myocardial infarctions. Determination of CK-MB, one of the three isoenzymes of CK, is important for the evaluation of the damage to the heart in the case of cardiac infarctions.

Most standard assays for a number of analytes, including creatine kinase, generally measure a change in ultraviolet light absorption. Light incident on the test sample can be either broad band radiation or filtered radiation, depending upon the optical equipment and procedure used.

It has been observed, however, that some compounds used in such assays are photosensitive, i.e. they change or promote changes prematurely in response to light. In particular, some dyes or dye precursors useful in assays (e.g. the triarylimidazole leuco dyes described above) exhibit undesirable photosensitivity in various assays, including assays for CK or other enzymes. As a result, the dyes or their precursors prematurely provide an unwanted optical density change and a high rate of background formation in the assay. In other words, there is an unwanted detectable change in rate. This problem was not recognized in assays of analytes which are present in high concentrations because the response from the analyte is so much greater than the unwanted background. However, the problem became pronounced in instances where the analyte is present in relatively low concentrations. A high rate of background formation significantly reduces assay sensitivity and precision.

While many photosensitive dyes or dye precursors are useful for assays of low level analytes, their use may be restricted due to their photosensitivity. Hence, it would be desirable to have a means for using such dyes in a highly sensitive assay without concern for their photosensitivity.

SUMMARY OF THE INVENTION

The problems noted above are overcome with a self-supporting analytical element comprising an absorbent carrier material containing an interactive composition for a clinically significant enzyme analyte comprising a photosensitive compound, and a filter layer comprising at least one filter dye and situated in relation to the carrier material such that incident radiation for detecting the density change passes through the filter layer prior to incidence upon the photosensitive compound.

In a preferred embodiment, a multilayer analytical element contains an interactive composition which is capable of providing an optical density change as a result of interaction with a clinically significant enzyme analyte, the interactive composition comprising a photosensitive compound, and comprises:

a support having thereon,
a filter layer comprising at least one filter dye and situated in relation to the interactive composition such that incident radiation for detecting the density change passes through the filter layer prior to incidence upon the photosensitive compound.

More specifically, this invention provides a multilayer analytical element for the determination of total creatine kinase or an isoenzyme thereof comprising an interactive composition which provides a detectable optical density change upon interaction with creatine kinase and comprises a photosensitive dye or dye precursor, and a nonporous support having thereon:

a layer containing said photosensitive dye or dye precursor,
a filter layer comprising at least one filter dye and situated in relation to the photosensitive dye layer such that incident radiation for detecting the density change passes through the filter layer prior to incidence upon the photosensitive dye layer, and
an outermost porous spreading layer.

A method for the determination of a clinically significant enzyme analyte comprises the steps of:

A. contacting a sample of a liquid suspected of containing a clinically significant enzyme analyte with an analytical element comprising an absorbent carrier material and an interactive composition which is capable of providing an optical density change as a result of interaction with the analyte and which comprises a photosensitive compound, and a filter layer comprising at least one filter dye and situated in relation to the photosensitive compound such that incident radiation for detecting the density change passes through the filter layer prior to incidence upon the photosensitive compound, and B. determining the optical density change resulting from the presence of the analyte.

The present invention provides a highly sensitive spectrophotometric assay for a clinically significant enzyme analyte of choice in which a photosensitive compound (e.g. a dye or precursor) is used. Clinically significant enzyme analyte is a term of art known to refer to those enzymes which are of interest in clinical evaluation of human or animal biological fluids. These enzymes are normally in biological fluids in measurable amounts.

The present invention overcomes the problems of unwanted background rate which are particularly severe in the detection of low level enzyme analytes. Determinations of isoenzymes, e.g. creatine kinase-MB, can be determined to advantage with this invention. The assay of the present invention provides improved precision, particularly in the determination of CK-MB.

The advantages of the present invention are attained by the use of a filter layer in the element of the invention. This layer contains one or more filter dyes which absorb unwanted electromagnetic radiation that would adversely affect photosensitive compounds in the element. Unwanted background rate of reaction is thereby reduced and precision is improved. Element keeping is also improved with use of the filter layer. The filter layer can be placed in any location in the element as long as it is situated in the path of incident radiation used to detect the optical density change resulting from analyte reaction. This incident radiation passes through the filter layer prior to reaching the photosensitive compound.

DETAILED DESCRIPTION OF THE INVENTION

Figure 1:
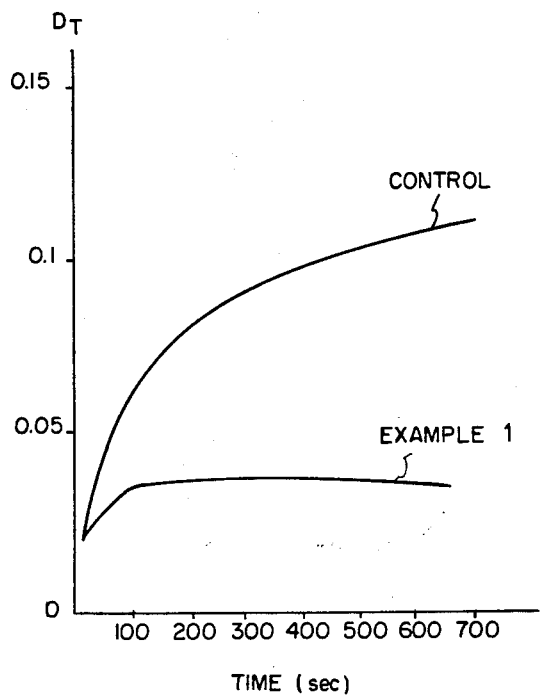
FIGS. 1 and 2 are graphical plots of transmission density ($D_T$) versus time for a measurement of premature formation of background as described in Examples 1 and 2 below.

The present invention relates to the determination (qualitative or quantitative measurement) of any of a wide number of clinically significant enzyme analytes which can be determined spectrophotometrically. Such analytes are generally present in test fluids at low levels, e.g. less than about 150 I.U./dl, and more particularly at less than about 50 I.U./dl. They include creatine kinase or an isoenzyme thereof, lipase, lactate dehydrogenase, aldolases, transaminases, and others known to one skilled in the art. This invention is particularly useful for the colorimetric determination of total creatine kinase or a creatine kinase isoenzyme in aqueous liquids.

The invention can be used to assay any aqueous fluid. It is particularly useful for the assay of animal or human biological fluids. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like. The preferred use of this invention is to determine an analyte in human blood serum. The test sample can be diluted or undiluted.

In a preferred embodiment, the present invention relates to an immunochemical method for selectively determining an isoenzyme of creatine kinase, e.g. creatine kinase-MB, in a biological fluid which also possibly contains CK-MM and CK-BB. The other isoenzymes can be similarly determined. Generally, the method of this invention comprises appropriately contacting the liquid to be assayed with the analytical element of this invention, the details of which are provided below. Prior to or simultaneously with that contact, for an assay of an isoenzyme, the liquid sample is contacted with one or more antibodies which are capable of either preferentially reacting with or preferentially inhibiting the enzymatic activity of the isoenzymes not of interest, e.g. the M subunits in the CK-MM and CK-MB isoenzymes present in the sample. In this example, the B subunit of the CK-MB isoenzyme is ideally uneffected by the presence of the antibodies, and therefore, are free to react in any of a number of reaction schemes to produce a detectable optical density change. The amount of CK-BB is generally considered negligible in such assays. The density change produced is then directly correlated to the amount of CK-MB isoenzyme in the fluid sample.

The method of this invention is carried out by measuring the optical density change generated as a result of the presence of the analyte when it is contacted and mixed with the reagents sufficient to produce the density change. In some cases, only a photosensitive dye or dye precursor described herein is needed to provide the optical density change. In preferred embodiments, additional reagents are in the element in the form of an interactive composition which, through one or more reactions, provides the optical density change in the presence of an analyte.

Photosensitive compounds which can be used in the method of this invention without concern about undesired photosensitive effects include any organic or inorganic compound which changes in some manner in response to electromagnetic radiation. For example, the compound could be a photosensitive dye or dye precursor which changes in optical density with incident radiation. Alternatively, the compound could be an electron transfer agent, cofactor, substrate, buffer, activator, antioxidant, etc. which changes, reacts or causes change in response to electromagnetic radiation.

Photosensitive dyes or dye precursors useful in the practice of this invention include all organic compounds which have the capability of absorbing or emitting a characteristic wavelength for detection, or which can be converted to such species. These materials are adversely sensitive to electromagnetic radiation, particularly that in the 200 to 700 nm region of the electromagnetic spectrum and exhibit an optical density change in response to that radiation.

Classes of useful photosensitive dyes and precursors include: cyanines, allopolarcyanines, triarylmethanes and imidazoles, particularly di- and triarylimidazole leuco dyes such as those described in U.S. Pat. No. 4,089,747, noted above, E.P. Application No. 122,641 and Jap. patent publication No. 58-045,557. The triarylimidiazole leuco dyes of U.S. Pat. No. 4,089,747 are preferred in the practice of this invention.

The remainder of the details of this invention will be illustrated as it applies to an assay for creatine kinase or an isoenzyme thereof. However, this invention is not limited in scope to these embodiments.

The density change for the determination of creatine kinase is detected spectrophotometrically, meaning as an optical density resulting from the reaction of creatine phosphate or its reaction product according to the reaction (1) in the forward direction:

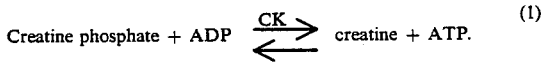

(1)

In its simplest form, the assay can measure either the disappearance of creatine phosphate, or the appearance of creatine.

Generally, however, reaction (1) is coupled with one or more other enzymatic reactions which provide an optical density change as a result of further reaction of ATP or its reaction product. The optical density change can be colorimetric, fluorometric, or photometric, and can be either a change from colorless to colored, a change from colored to colorless, a change in the rate of increase or decrease in optical density, or a shift in absorbance from one wavelength to another.

More particularly, total CK or an isoenzyme, e.g. CK-MB, is determined by colorimetric means whereby an optical density change is measured at a wavelength between about 200 and about 900 nm.

In this embodiment, the optical density change is provided by a photosensitive dye or dye precursor which reacts with the byproducts of the reaction of the analyte with an interactive composition.

In a preferred embodiment of the present invention, total CK or CK-MB activity is determined by the following sequence of reactions:

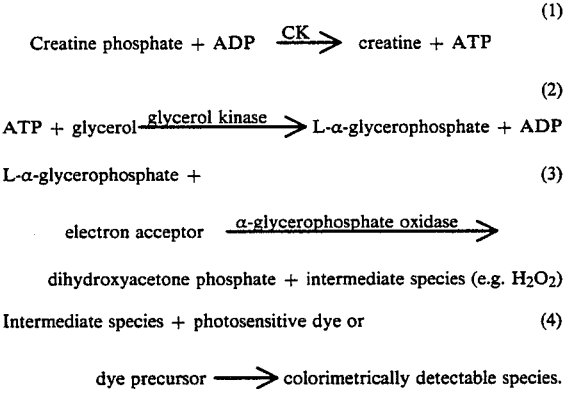

Quantification of total creatine kinase or its isoenzyme in the practice of this preferred embodiment is achieved using oxygen as the electron acceptor, a substance having peroxidative activity, and a photosensitive chromogen. In such a case, reaction (3) produces dihydroxyacetone phosphate and hydrogen peroxide. The details of this sequence of reactions are provided in U.S. Pat. No. 4,547,461 (issued Oct. 15, 1985 to Esders et al).

Useful peroxidative substances include peroxidase. A peroxidase is an enzyme which will catalyze a reaction wherein hydrogen peroxide oxidizes another substance. The peroxidases are generally conjugated proteins containing iron porphyrin. Peroxidase occurs in horseradish, potatoes, fig tree sap and turnips (plant peroxidase), in milk (lacto peroxidase), and in white blood corpuscles (verdo peroxidase). It also occurs in microorganisms and can be produced by fermentation. Certain synthetic peroxidases, such as those disclosed by Theorell and Maehly in *Acta chem. Scand.*, Vol. 4, pages 422-434 (1950), are also useful. A preferred peroxidase is that obtained from horseradish. Other peroxidative substances are known in the art.

Photosensitive chromogens which provide color formation in the presence of hydrogen peroxide and peroxidase useful in the present invention are described above. Leuco dyes are particularly useful including those described in the references noted above. Particularly useful leuco dyes include 2-(3,5-dimethoxy-4-hydroxyphenyl)-4,5-bis(4-dimethylaminophenyl-)imidazole, 2-(4-hydroxy-3-methoxyphenyl)-4,5-bi(p-dimethylaminophenyl)-1H-imidazole, 2-(3-ethoxy-4-hydroxyphenyl-4,5-bis(p-dimethylaminophenyl)-1H-imidazole, 2-(4-hydroxy-3,5-dimethoxyphenyl)-4-[4-(dimethylamino)-phenyl]-5-(2-furyl)imidazole, 2-(4-hydroxy-3,5-dimethoxyphenyl)-4,5-di(2-furyl-)imidazole, 2-(3,5-dimethoxy-4-hydoxyphenyl)-4-[4-(dimethylamino)phenyl]-5-phenethylimidazole and 2-(3,5-dimethoxy-4-hydroxyphenyl)-4-[4-(dimethylamino)phenyl]-5-benzylimidazole.

The amounts of the reagents, substrates and enzymes useful in the practice of this invention, including the photosensitive dyes or dye precursors, are dependent to a large extent upon the concentration of enzyme analyte (e.g. creatine kinase or isoenzyme) in the sample, the sophistication of the detection apparatus, and the detectable change produced. The amounts are readily determinable by one skilled in clinical chemistry having the teachings of the references noted above before him.

The analytical element of this invention can also include other reagents or addenda generally used in total CK or CK isoenzyme determinations, including CK activators, adenylate kinase inhibitors, metal ion cofactors (e.g. magnesium calcium and iron ions), solvents, buffers, surfactants, etc. It is particularly desirable to include one or more CK activators which promote full creatine kinase activity. Such activators include mercapto-containing compounds (also known as thiol-containing or sulfhydryl compounds), such as thioglucose, dithiothreitol, dithioerythritol, mercaptoethanol, glutathione, N-acetylcysteine, cysteine, thioglycerol, thioglycolic acid, etc. in amounts known to one skilled in clinical chemistry.

Antibodies useful in the practice of this invention to determine a CK isoenzyme can be specific to either B or M subunits and can be generated from antisera using known procedures. The antibodies are generally used on a suitable carrier. In the assay of this invention, one or more antibodies can be immobilized within the element itself, if desired, without any additional carrier material or added prior to or simultaneously with the test sample to the element during the assay. Further details of useful antibodies for CK-MB determinations and carrier materials are provided, for example, in U.S. Pat. Nos. 4,237,044 (issued Dec. 2, 1980 to Wurzburg et al) and 4,260,678 (issued Apr. 7, 1981 to Lepp et al).

The element of this invention comprises at least two layers which can be self-supporting, i.e. having sufficient integral strength to remain intact during an assay. More generally, it comprises a nonporous support having thereon a first layer containing a photosensitive compound and a filter layer described herein. The layer containing the photosensitive compound generally comprises one or more binder materials in which the compound is distributed. Useful binder materials are known to one skilled in the art and include hardened or unhardened gelatin and other colloidal materials, polysaccharides, natural and synthetic polymers, etc.

Alternatively, the photosensitive compound can be in the porous spreading layer (described above) of an element.

Similarly, the filter layer contains one or more filter dyes in one or more binder materials. The filter dyes used are chosen based upon their solubility in the binder, their extinction coefficient, the wavelengths of absorption and other parameters known to one skilled in the art. A mixture of such dyes can be used to absorb desired wavelengths. In a preferred embodiment, the filter dyes filter out radiation having a wavelength shorter than about 500 nm. Examples of useful dyes are disperse textile dyes, ultraviolet light absorbers as known in the art. Examples of useful filter dyes include C.I. Disperse Red 137, C.I. Disperse Yellow 5, C.I. Disperse Orange 3 and 2,2'-dihydroxy-4,4'-dimethoxybenzophenone and others known in the art. All of these dyes are available commercially.

The amounts of filter dyes in the filter layer can be determined readily by a skilled worker in the art. The amount of each dye to be used depends upon the dye's extinction coefficient, its solubility in the binders used and the proportions needed to absorb the desired wavelengths. These amounts can be determined with routine experimentation.

The filter dyes can be used in a suitable binder material in which they are soluble and which can be suitably applied or otherwise incorporated into the element. Generally the binders are synthetic or natural polymeric or colloidal materials, e.g. gelatin, agar, collagen, cellulose esters (e.g. cellulose acetate), polystyrene, polyurethane, polycarbonates, and the like. Cellulose acetate is preferred in the practice of this invention.

Alternatively, the filter layer can also serve as a nonporous support. The only critical aspect of the filter layer is that it is situated in relation to the photosensitive compound such that incident radiation used to detect the optical density change passes through the filter layer before reaching the photosensitive compound. The filter layer can be incorporated into the element simultaneously with preparation of the other layers. Alternatively, the other layers can be prepared first and the filter layer later applied to them in some manner, e.g. coating or lamination.

More preferably, the element also includes a porous spreading layer as the outermost layer. Reagents and/or antibodies for isoenzyme determination can be incorporated into the porous spreading layer by imbibition, impregnation, coating or another suitable technique. Generally, they are incorporated into a coating composition, whereas antibodies are incorporated by imbibition or wash coating into an already coated layer. Useful absorbent materials for making porous spreading layers are insoluble and maintain their structural integrity when exposed to water or biological fluids such as whole blood or serum. Useful elements can have spreading layers prepared from paper, porous particulate structures, porous polymeric films, cellulose, wood, glass fibers, woven and nonwoven fibrous fabrics (synthetic and nonsynthetic) and the like. Useful materials and procedures for making such layers are well known in the art.

For example, the porous spreading layer can be prepared from any suitable fibrous or non-fibrous material or mixtures of either or both including those described in U.S. Pat. Nos. 4,292,272 (issued Sept. 29, 1981 to Kitajima et al), 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese patent publication No. 57(1982)-101760 (published June 24, 1982). The spreading layer should be isotropically porous, meaning that the porosity is the same in each direction in the layer as caused by interconnected spaces or pores between particles, fibers, polymeric strands, etc.

The support can be any suitable dimensionally stable and nonporous, and preferably transparent (i.e. radiation transmissive) material which transmits electromagnetic radiation of a wavelength between about 200 and about 900 nm. A support of choice for a particular element should be compatible with the intended mode of detection (reflection, transmission or fluorescent spectroscopy). Useful supports can be made from paper, metal foils, polystyrene, polyesters [e.g. poly(ethylene terephthalate)], polycarbonates, cellulose esters (e.g. cellulose acetate), etc.

The element of this invention can have a registration or reagent layer under the porous spreading layer. These layers can contain one or more reagents or enzymes needed for the assay, surfactants, buffers, etc.. They generally contain one or more hydrophilic binder materials (e.g. treated or untreated gelatin and other colloidal materials, polysaccharides, vinyl pyrrolidone polymers, acrylamide polymers, etc.). Examples of other binder materials are known to one skilled in the art. Preferably, the layer contains gelatin which has been hardened with a standard hardener.

The elements can have one or more other layers, e.g. additional spreading layers, radiation-blocking or filter layers, subbing layers, barrier layers, etc. The layers are generally in fluid contact with each other, meaning that fluids, reagents and reaction products can pass or be transported between superposed regions of adjacent layers by fluid.

A preferred embodiment of this invention is a multilayer element useful for determining CK-MB comprising a support having thereon, in order and in fluid contact on one side, a registration layer containing a photosensitive dye precursor (leuco dye) described herein and optionally other reagents, a reagent layer containing creatine phosphate, AMP, ADP and other desired reagents, optionally a subbing layer, and a porous spreading layer which optionally contains either a CK activator or at least one antibody for the M subunits of CK or both. The subbing layer can comprise one or more subbing materials known to one skilled in the art, e.g. vinyl pyrrolidone polymers, acrylamide polymers, and the like.

When the preferred photosensitive dye precursor described above is used, the registration layer also contains α-glycerophosphate oxidase, and the reagent layer also contains glycerol and glycerol kinase.

On the other side of the support is a filter layer, described above, through which incident light passes prior to incidence upon the registration layer.

A variety of different elements, depending on the method of assay, can be prepared in accordance with the present invention. Elements can be configured in a variety of forms, including elongated tapes of any desired width, sheets, slides or chips. The assay of this invention can be manual or automated. In general, in using the dry elements, analyte determination is made by taking the element from a supply roll, chip packet or other source and physically contacting it with a sample (e.g. 1–200 μl) of the liquid to be tested so that the sample mixes with the reagents within the element. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

In the case of CK or an isoenzyme, CK or isoenzyme in the test sample catalyzes reaction of the ADP with the creatine phosphate substrate at a rate based on the amount of analyte present in the sample. The rate of optical density change (e.g. dye formation) due to either reaction of creatine phosphate or formation of the reaction product (e.g. ATP) is quantifiable by passing the element through a zone in which suitable detection apparatus for reflection or transmission spectrophotometry is provided. Suitable detection apparatus and procedures are known in the art.

In the following examples, illustrating the practice of this invention, the materials used were obtained as follows: ESTANE 5715 polyurethane resin from B. F. Goodrich (Cleveland, Ohio, U.S.A.), TRITON X-200E and X-405 surfactants from Rohm & Haas (Philadelphia, Pa, U.S.A.), magnesium acetate from Allied Chemical Corp. (Morristown, N.J., U.S.A.), glycerol kinase from Worthington (Freehold, N.J., U.S.A.), AMP, ADP and DAPP from Sigma Chemical Co. (St. Louis, Mo., U.S.A.), creatine phosphate from Calbiochem (San Diego, Calif., U.S.A.), ALKANOL XC from DuPont (Wilmington, Del., U.S.A.), horseradish peroxidase from Miles laboratories (Elkhart, Ind., U.S.A.), α-glycerophosphate oxidase from Toyo Jozo (Shizuoka-Keu, Japan), UVINOL 490 ultraviolet filter dye from Polychrome Corp. (Clark, N.J., U.S.A.), and the remainder either from Eastman Organic Chemicals (Rochester, N.Y., U.S.A.) or prepared using known procedures and starting materials.

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme.

EXAMPLES 1 and 2

ASSAY OF CREATINE KINASE-MB

In these examples, the amount of undesired rate of change in optical density was measured with an element of this invention. CK-MB was also determined in pooled human serum using the element. The assay of this invention was compared to an assay carried out with a known analytical element which is outside the scope of this invention.

The elements used in this comparison had the general format and components shown below. The Control element, however, did not have a filter layer. They were prepared like the element described in U.S. Pat. No. 4,547,461, noted above except that it also contained anti-CK-MM antibodies in the spreading layer. The element of this invention comprised a filter layer having the composition shown below and coated on the backside of the support.

| Layer | Component | Amount |
|---|---|---|
| Spreading Layer | Goat anti-human CK-MM | 5,000–300,000 U/m²** |
| | TiO₂ | 20–80 g/m² |
| | Cellulose acetate | 2–10 g/m² |
| | ESTANE 5715 resin | 1–4 g/m² |
| | N—acetyl-L-cysteine | 0.2–0.6 g/m² |
| | TRITON X-405 surfactant | 0.5–3 g/m² |
| | Ethylenebis(oxyethylenenitrilo)tetraacetic acid | 0.2–0.8 g/m² |
| Subbing Layer | Poly(N—isopropylacrylamide) | 0.2–0.6 g/m² |
| Reagent Layer | Gelatin (Hardened) | 2–8 g/m² |
| | Magnesium acetate | 0.2–2 g/m² |
| | TRITON X-200E surfactant | 0.005–0.5 g/m² |
| | Adenosine-5'-diphosphate (ADP) | 0.04–0.2 g/m² |
| | Glycerol kinase | 2,000–10,000 I.U./m² |
| | Adenosine-5'-monophosphate (AMP) | 0.2–2 g/m² |
| | Creatine phosphate | 1–4 g/m² |
| | P¹,P⁵-di(adenosine-5')-pentaphosphate (DAPP) | 0.01–0.1 g/m² |
| | Glycerol | 0.1–0.3 g/m² |
| | 2-[Bis(2-hydroxyethyl)amino-2-(hydroxymethyl)-1,3-propanediol | 1–5 g/m² |
| Registration Layer | Gelatin (Hardened) | 10.8 g/m² |
| | 2-[Bis(2-hydroxyethyl)-amino]-2-(hydroxymethyl)-1,3-propanediol | 1–5 g/m² |
| | ALKANOL XC surfactant | 0.1–0.5 g/m² |
| | Peroxidase | 10,000–50,000 I.U./m² |
| | 2-(3,5-dimethoxy-4-hydroxyphenyl)-4,5-bis(4-dimethylaminophenyl)imidazole | 0.1–0.3 g/m². |
| | Ascorbic acid oxidase | 6,000–12,000 I.U./m² |
| | L-α-Glycerophosphate oxidase | 1,000–10,000 I.U./m² |
| | Glycolic acid | 0.1–0.5 g/m² |
| | 5,5-Dimethyl-1,3-cyclohexanedione | 0.01–5 g/m² |
| | TRITON X-200E surfactant | 0.05–1 g/m² |
| | 2,4-Di-n-pentylphenol | 1–3 g/m² |
| | Poly(ethylene terephthalate) Support | |

*The antisera level is given in Units (U) which are defined by the titer assay: (50% inhibition titer) (ml/0.093 m²) = U/m².

The element of the present invention comprised a filter layer coated adjacent to the support on the side opposite the other element layers. This filter layer contained the following materials: cellulose acetate binder (5–15 g/m²), UVINOL 490 ultraviolet filter dye (0.2–0.4 g/m²), C.I. Disperse Orange 3 (EASTONE Orange 2R) filter dye (0.1–0.2 g/m²), C.I. Disperse Yellow 5 (EASTONE Yellow 6GN) filter dye (0.3–0.4 g/m²) and C.I. Disperse Orange 3 (EASTONE Red 2B-GLF) filter dye (0.1–0.2 g/m²).

The elements (both Control and invention) were evaluated by applying a 10 μl sample of either distilled water or pooled human serum to the spreading layer, incubating at 37° C. for up to 12 minutes, and measuring the change in reflection density resulting from dye formation with a spectrophotometer.

Figure 2:
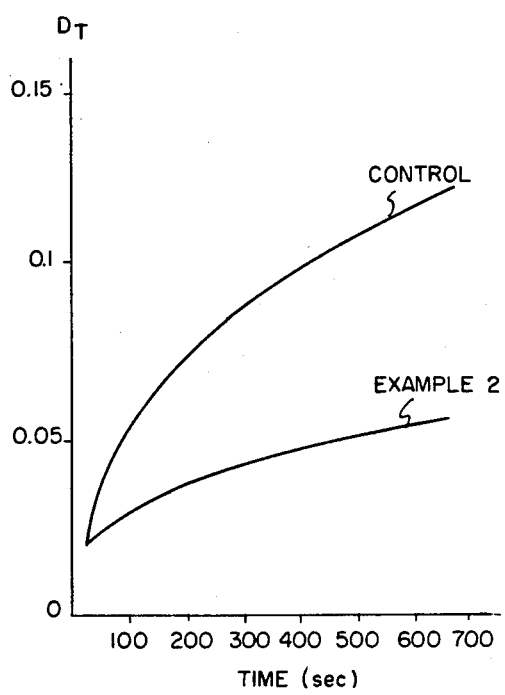

Reflection density readings were transformed into transmission density ($D_T$) readings using Clapper-Williams transforms [described in *J. Opt. Soc. Am.*, 43, 595 (1953)]. A plot of transmission density versus time was made for each element. The results are shown in FIGS. 1 and 2. FIG. 1 shows the background rate when the Control and invention elements were spotted with distilled water, whereas FIG. 2 shows the background rate when the elements were spotted with pooled human serum. It can be seen that the Control element (absent a filter layer) exhibited a high background rate while the element of the present invention exhibited a significantly lower background rate. Both figures show the magnitude of the background rate change between the Control element and the element of the present invention.

EXAMPLE 3

ALTERNATIVE ANALYTICAL ELEMENT

Figure 3:
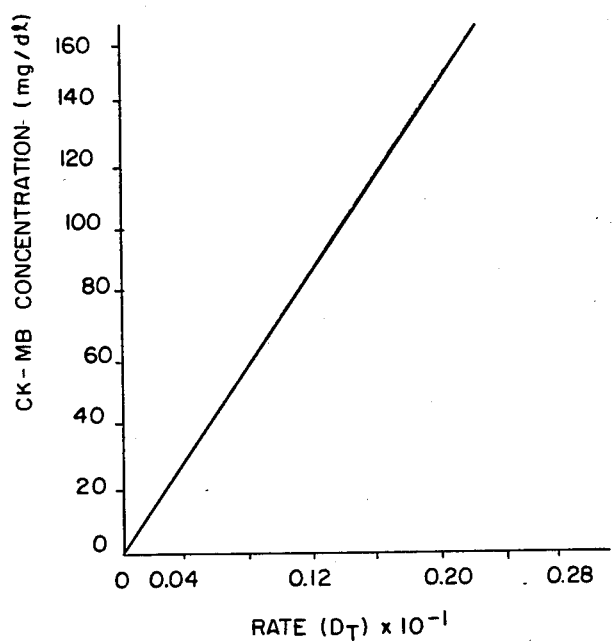
FIG. 3 is a calibration curve of CK-MB concentration versus rate of reaction $\times 10^{-1}$ as described in Example 3 below.

Another element of the present invention was prepared similar to that shown in Examples 1 and 2 except that the filter layer was applied to the support adjacent to the registration layer. The element was evaluated as described in Example 1 and a calibration curve was generated using standard procedures by applying samples having predetermined amounts of CK-MB. This curve is shown in FIG. 3.

EXAMPLE 4

ASSAY FOR CREATINE KINASE-MB

An assay for CK-MB was carried out using an element and the procedures described in Examples 1 and 2 above. The Control element of Examples 1 and 2 was similarly tested. The elements were spotted with two test solutions: pooled human serum containing CK-MB (about 300 I.U./1 CK-MB), and a bovine serum albumin (BSA) solution containing about 2000 I.U./1 CK-MM and about 40 I.U./1 CK-MB.

From the reflection density results obtained, precision of both assays was calculated for both test samples. The precision results are shown in Table I below. It is evident that the assay of the present invention is more precise with both test samples than the assay using the Control element.

TABLE I

| Element | Test Solution | Early Read % C.V.* | Late Read % C.V.* |
|---|---|---|---|
| Control | Human Serum | 2.5 | 1.9 |
| Control | BSA | 14.6 | 16.3 |
| Example 4 | Human Serum | 1.2 | 0.8 |
| Example 4 | BSA | 6.1 | 5.5 |

*% C.V. = % coefficient of variation. The early read was made after about 4 minutes into the assay, and the late read was made after about 5.6 minutes into the assay.

The invention has been described in detail with particular reference to preferred embodiments thereof, but it will be understood that variations and modifications can be effected within the spirit and scope of the invention.

We claim:
1. A self-supporting analytical element comprising:
   a layer comprising an absorbent carrier material containing an interactive composition for a clinically significant enzyme analyte, said composition comprising a photosensitive compound capable of providing a detectable optical density change at a predetermined characteristic wavelength in response to reaction of the analyte with its substrate, and
   a filter layer containing at least one filter dye selected to absorb incident radiation other than radiation at said characteristic wavelength produced in response to a reaction of the analyte with its substrate.

2. The element of claim 1 wherein said photosensitive compound is a photosensitive dye or dye precursor.

3. The element of claim 2 wherein said photosensitive dye precursor is an imidazole leuco dye.

4. A multilayer analytical element comprising
   a nonporous support having thereon two or more layers, and contained in at least one of said layers, an interactive composition for a clinically significant enzyme analyte, said composition comprising a photosensitive dye or dye precursor capable of providing a detectable optical density change at a predetermined characteristic wavelength in response to action of said analyte on a substrate,
   at least one of said layers being a porous spreading layer, and a second being a filter layer containing at least one filter dye selected to absorb incident radiation other than radiation at said predetermined characteristic wavelength produced in response to a reaction of the analyte with the substrate.

5. The element of claim 4 wherein said support is transparent to incident radiation and said photosensitive dye or dye precursor is in a layer located on the opposite side of said support from said filter layer.

6. The element of claim 4 wherein said filter layer is located between said support and a layer containing said photosensitive dye or dye precursor.

7. The element of claim 4 wherein said photosensitive dye precursor is an imidazole leuco dye.

8. A multilayer analytical element for the determination of creatine kinase or an isoenzyme thereof comprising a nonporous transparent support having thereon three or more layers including a filter layer, and contained in at least one of said layers other than said filter layer, an interactive composition for creatine kinase, said composition comprising one or more reagents which cumulatively provide a detectable optical density change at a predetermined characteristic wavelength in response to action of creatine kinase on a substrate, one of said reagents being a photosensitive dye or dye precursor,
   said support having on one side:
      said filter layer containing at least one filter dye selected to absorb incident radiation other than radiation at said predetermined characteristic wavelength, produced in response to a reaction of creatine kinase or an isoenzyme thereof with its substrate and
   on the other side, in order, two or more layers including:
      a layer containing said photosensitive dye or dye precursor, and
      an outermost porous spreading layer.

9. The element of claim 8 wherein said photosensitive dye precursor is a triarylimidazole leuco dye.

10. The element of claim 8 wherein said interactive composition further comprises the reagents creatine phosphate, adenosine-5'-diphosphate, glycerol, glycerol kinase and α-glycerophosphate oxidase, which reagents are located in any of said layers other than said filter layer.

11. The element of claim 8 further comprising creatine kinase-M antibodies immobilized in said porous spreading layer.

12. The element of claim 8 wherein said filter layer contains filter dyes cumulatively capable of filtering incident radiation having a wavelength of about 500 nm or less.

13. A method for the determination of a clinically significant enzyme analyte comprising the steps of:
   A. contacting a sample of a liquid suspected of containing a clinically significant enzyme analyte with an analytical element comprising:
      a layer comprising an absorbent carrier material containing a substrate and an interactive composition for said analyte, said composition comprising a photosensitive compound which is capable of providing an optical density change at a predetermined characteristic wavelength in response to action of said analyte on said substrate, and
      a filter layer comprising at least one filter dye selected to absorb incident radiation other than radiation at said characteristic wavelength,
      to produce an optical density change detectable at said predetermined characteristic wavelength as a result of the presence of said enzyme in said sample, and
   B. determining said optical density change at said predetermined characteristic wavelength by directing incident radiation from transmission, reflection or fluorescent spectrophotometry to said element in such fashion that said incident radiation passes through said filter layer before it reaches said absorbent layer.

14. A method for the determination of total creatine kinase or an isoenzyme thereof comprising the steps of:
   A. contacting a sample of a liquid suspected of containing creatine kinase or an isoenzyme thereof with a multilayer analytical element comprising a nonporous transparent support having thereon three or more layers including a filter layer, and contained in at least one of said layers other than said filter layer, a substrate and an interactive composition for creatine kinase, said composition comprising one or more reagents which cumulatively provide a detectable optical density change at a predetermined characteristic wavelength in response to action of creatine kinase on said substrate, one of said reagents being a photosensitive dye or dye precursor,
      said support having on one side:
         said filter layer containing at least one filter dye selected to absorb incident radiation other than radiation at said predetermined characteristic wavelength, produced in response to a reaction of creatine kinase or an isoenzyme thereof with its substrate and
      on the other side, in order, two or more layers including:
         a layer containing said photosensitive dye or dye precursor, and
         an outermost porous spreading layer, to produce an optical density change detectable at said predetermined characteristic wavelength as a result of the presence of creatine kinase or an isoenzyme thereof in said sample, and
   B. determining said optical density change at said predetermined characteristic wavelength by directing incident radiation from transmission or reflection spectrophotometry to said element in such fashion that said incident radiation passes through said filter layer before it reaches said photosensitive dye or dye precursor layer.

15. The method of claim 14 wherein said filter layer comprises one or more filter dyes which are capable of filtering incident radiation having a wavelength of about 500 nm or less and said detectable optical density change is determined at a predetermined characteristic wavelength of greater than 500 nm.

16. The method of claim 14 for the determination of creatine kinase-MB wherein said element comprises creatine kinase-M antibodies immobilized in its porous spreading layer.

17. The method of claim 14 wherein said photosensitive dye is a triarylimidiazole leuco dye and said interactive composition comprises adenosine-5'-diphosphate, glycerol, glycerol kinase and α-glycerophosphate oxidase.

18. The method of claim 17 wherein said triarylimidazole leuco dye is 2-(3,5-dimethoxy-4-hydroxyphenyl)-4,5-bis(4-dimethylaminophenyl)imidazole.

19. A multilayer analytical element for the determination of creatine kinase or an isoenzyme thereof comprising a nonporous transparent support having thereon three or more layers including a filter layer, and contained in at least one of said layers other than said filter layer, an interactive composition for creatine kinase, said composition comprising one or more reagents which cumulatively provide a detectable optical density change at a predetermined characteristic wavelength in response to action of creation kinase on a substrate, one of said reagents being a photosensitive dye or dye precursor,
   said support having on one side, in order, three or more layers including:
      said filter layer containing at least one filter dye selected to absorb incident radiation other than radiation at said predetermined characteristic wavelength, produced in response to a reaction of creatine kinase or an isoenzyme thereof with its substrate and
      a layer containing said photosensitive dye or dye precursor, and
      an outermost porous spreading layer.

20. A multilayer analytical element for the determination of creatine kinase or an isoenzyme thereof comprising a nonporous support having thereon three or more layers including a filter layer, and contained in at least one of said layers other than said filter layer, an interactive composition for creatine kinase, said composition comprising one or more reagents which cumulatively provide a detectable optical density change at a predetermined characteristic wavelength in response to action of creatine kinase on a substrate, one of said reagents being a photosensitive dye or dye precursor,
   said support having on one side, in order, three or more layers including:
      a layer containing said photosensitive dye or dye precursor,
      said filter layer containing at least one filter dye selected to absorb incident radiation other than radiation at said predetermined characteristic wavelength, produced in response to a reaction of creatine kinase or an isoenzyme thereof with its substrate and
      an outermost porous spreading layer.

* * * * *